United States Patent [19]

Katims

[11] Patent Number: 5,078,678
[45] Date of Patent: Jan. 7, 1992

[54] METHOD AND APPARATUS FOR LOCATING A CATHETER ADJACENT TO A PACEMAKER NODE OF THE HEART

[76] Inventor: Jefferson Katims, 145 E. 16th St., New York, N.Y. 10003

[21] Appl. No.: 487,296

[22] Filed: Mar. 2, 1990

[51] Int. Cl.$^5$ ............................................... A61B 5/02
[52] U.S. Cl. ..................................... 604/28; 128/734; 604/117
[58] Field of Search ......................... 604/117, 158, 28; 128/734, 737, 662.06, 653

[56] References Cited

U.S. PATENT DOCUMENTS

| | | | |
|---|---|---|---|
| 4,224,949 | 9/1980 | Scott et al. | 128/734 |
| 4,380,237 | 4/1983 | Newbower | 128/734 |
| 4,431,005 | 2/1984 | McCormick | 128/653 |
| 4,674,518 | 6/1987 | Salo | 128/734 |
| 4,697,595 | 10/1987 | Breyer et al. | 128/662.06 |
| 4,781,685 | 11/1988 | Lehmann et al. | 604/117 |
| 4,821,731 | 4/1989 | Martinelli et al. | 128/653 R |
| 4,836,214 | 6/1989 | Sramek | 128/734 |
| 4,852,580 | 8/1989 | Wood | 128/734 |
| 4,901,725 | 2/1990 | Nappholz et al. | 128/734 |
| 4,905,693 | 3/1990 | Strohl, Jr et al. | 128/653 R |

*Primary Examiner*—Paul J. Hirsch
*Attorney, Agent, or Firm*—Karl W. Flocks

[57] ABSTRACT

A method and apparatus for locating a catheter adjacent to a pacemaker node of the heart. The placement of a catheter tip just before SA heart pacemaker node is a common and desired procedure in medicine, with the most serious complication being its accidental advancement of the beyond this point placing its tip into the heart, with often fatal complications. The catheter tip location just before SA heart pacemaker node is desired because is most often the safest and optimal location. The catheter described in the present invention is placed by a physician within a patients body circulatory vessel and advanced towards the heart SA pacemaker node, using traditional medical procedures. From the distal tip of the catheter the endogenous electrical activity from the SA pacemaker node of the heart is monitored and transmitted via at least one insulated transmission line located within the catheter to an electronic catheter monitoring system located outside the body. As the catheter is advanced its tip moves within the patient's circulatory vessel. Simultaneously, the electronic catheter monitoring system monitors the natural pacemaker node potentials, obtained at the tip of the catheter, which increase as the node is approached and decrease as the node is passed. The electronic catheter monitoring system display indicates these monitored changes to the physician advancing the catheter. The information provided by the electronic catheter monitoring system is used by the physician to guide catheter placement and confirm its location at the desired location outside the heart before the SA node.

6 Claims, 3 Drawing Sheets

- ○ ADVANCE
- ○ BACK-UP
- ● STOP-CORRECT PLACEMENT (PROXIMAL TO S.A. NODE)

P WAVES

P WAVES

P WAVES

P WAVES

METHOD AND APPARATUS FOR LOCATING A CATHETER ADJACENT TO A PACEMAKER NODE OF THE HEART

Disclosure documents relating to the present invention filed with the U.S. Patent and Trademark Office:
U.S. Pat. No. 154905 Aug. 19, 1986
U.S. Pat. No. 190679 Feb. 2, 1988
U.S. Pat. No. 216792 Dec. 23, 1988

FIELD OF THE INVENTION

The present invention relates to a method and apparatus for locating a catheter tip within the superior vena cava (one of the major veins leading into the heart) in the region of the junction of the superior vena cava and the atrium proper on the heart. The endogenous electrical potentials from the cardiac Sinoatrial pacemaker node are monitored from the tip of this catheter to provide a reference location for the placement of the catheter. A pacemaker node in cardiology is defined as a group of cells that automatically generates voltage potentials that may spread to other regions of the heart. The present invention is not imaging but relates to the local environment of the catheter tip.

1. Background of the Invention

It is a standardized and optimal method in the practice of medicine today to place a "central venous catheter" (CVC) tip within the superior vena cava in the region of the junction of the superior vena cava and the atrium proper of the heart. This area has among the greatest volume of venous blood flow in the body outside the heart which maximizes drug dilution and makes it the safest place in the circulatory system to administer most medications. When a catheter or probe is being placed in a human body, there is generally no aid in determining the path of the placement other than by intimate knowledge of the body part and by touch and feel or extraction of bodily fluid. A X-ray, sonogram or similar diagnostic device, however, is used to confirm the location of a CVC for example, near the heart so as to rule out accidental placement into the heart which is often lethal, or into a lung, which often causes another serious complication such as a collapsed lung (pneumothorax). The time required of such X-ray confirmation delays the use of such a central line catheter even in life threatening situations, and also impinges on the time necessary to prevent ultimate death in a patient resulting from a catheter tip that has perforated the wall of the heart during the placement procedure. According to a July 1989 U.S. Food and Drug Administration report, there are approximately 3 million CVC placement procedures conducted annually in the United States and it has been estimated that "complications occur in 5% to 20% these procedures (1). This report further states, " the catheter tip should not be placed in, or allowed to migrate into the heart (from within a major vessel, a vessel or blood vessel or circulatory vessel is defined as a vein or artery). Catheter tip position should be confirmed by x-ray or other imaging modality and be rechecked periodically. Central venous catheterization must be performed by trained personnel well-versed in anatomical land marks, safe technique, and potential complications."The most serious life threatening complications occur from the inadvertent placement of a CVC beyond the superior vena cava into the heart.

2. Description of the Prior Art

The remote monitoring of the electrical characteristics of the human body and heart (electrocardiogram, EKG) through percutaneously implanted electrical devices is well-known. The EKG in the heart is generated by naturally occurring pacemaker nodes within the heart. U.S. Pat. No. 4,552,127 issued to Schiff on Nov. 12, 1985, U.S. Pat. No. 4,624,265 issued to Grassi on Nov. 25, 1986 and U.S. Pat. No. 4,637,404 issued to Gessman on Jan. 20, 1987 all describe such devices. None of this prior art teaches a method and apparatus for preventing the accidental placement of a CVC within the heart as well permitting periodic or continuous monitoring and confirmation of the CVC location.

SUMMARY OF THE INVENTION

It is an object of the present invention to provide a system and a method to assist in preventing the accidental placement of a CVC within the heart as well permitting periodic or continuous monitoring and confirmation of the CVC location.

This method assists in the placement of a medical probe; catheter or other tubular or rod shaped medical device within the superior vena cava in the region of the junction of the superior vena cava and the atrium proper of the heart. This method confirms placement by determining and monitoring endogenously pacemaker generated local electrical potential characteristics of body tissue in the region of the tip of the catheter. These electrical characteristics are primarily brought about by dynamic changes in the ion permeability of pacemaker cell membranes to electrolytes in body fluid such as sodium and potassium. These biological changes in the cellular ion concentrations across membranes result in the generation of endogenous electrical potentials.

In accordance with the above objects and other objects which will become apparent hereinafter, there is provided a monitoring system for assisting in the characterization of the monitored endogenous electrical potentials in the region of the tip of the catheter. The catheter or probe will hereafter be referred to as a "catheter". The term "tissue" will be used hereafter to refer to any tissue within a body. A catheter contains the means for sensing the appropriate electrical characteristics of the tissue at the distal end of the catheter and transmitting the signal to the proximal end. This means for sensing which transmits the tissue electrical characteristics through the electrical catheter between its proximal end which may be located outside the body and the distal end which may be inserted inside the body will here after be referred to as a "transmission line". Additional transmission lines may also be in circuit between the tissue of the subjects body and the electrical monitoring system. All transmission lines are insulated from monitoring electronic signals to the tissue which they contact except at their distal ends. This site will hereafter be referred to as the "transmission contact area". The transmission line may be as simple as a conductor. Additionally, this transmission line may be composed of a fluid within a tube within a catheter; for example, an electrolyte containing solution may be used as a conductor.

In the simplest case the electrical catheter localization system, employing a catheter with only a single transmission line must also employ a transmission line which is in electrical connection with the skin of the subject being catheterized. This additional transmission line is not strictly required when a catheter is employed which has more than one transmission line. The electrical catheter localization system, in circuit with an electrical catheter requires a minimum of one transmission line within the catheter. The electronic catheter localization system continuously monitors the characteristics and signals relating to endogenous electrical potentials from the transmission contact area located at the tip of the catheter as the catheter is moved through circulatory vessels.

Furthermore, this method may also be employed with standard multi-lumen (lumen, i.e., the passage within a tube) catheters by electrically monitoring from the external catheter ports of lumens filled with an electrolyte containing solution (eg. blood or saline). An electrolyte filled lumen within a catheter, enables such an application ie., by serving as an electrical conducting medium within the lumen conducting between its opening at the catheter tip and its external port. This enables the catheter tip opening to function as a local electrode, and the catheter itself serves as the insulator of this electrode. These tip located electrodes allow the monitoring of the electrical potentials in the region of the tissue close to the tip of the catheter. This provides unique and practical information to the practitioner by indicating whether an inserted catheter is approaching or moving away from a source of endogenous electrical potentials within the body such as a pacemaker node within the heart. This method of monitoring the electrical characteristics of a cardiac pacemaker node from the catheter tip as the catheter is being inserted enables the determination of the location of the tip with respect to the pacemaker node, and is part of the invention of this present disclosure. Furthermore, this method may be applied to move an already inserted CVC to confirm that its position is correct.

The present invention will be better understood and the objects and important features, other than those specifically set forth above, will become apparent when consideration is given to the following details and description, which when taken in conjunction with the annexed drawings, describes, discloses, illustrates, and shows preferred embodiments or modifications of the present invention and what is presently considered and believed to be the best mode of practice in the principles thereof, other embodiments or modifications may be suggested to those having the benefit of the teachings herein, and such other embodiments or modifications are intended to be reserved especially as they fall within the scope and spirit of the subjoined claims.

BRIEF DESCRIPTION OF THE DRAWINGS

FIGS. 2A, 28, 2C, and 2D are traces of monitored pacemaker generated electrical potentials from the electrical monitoring system located in FIG. 1 from various electrical catheter tip locations.

DETAILED DESCRIPTION OF THE PREFERRED EMBODIMENTS

Figure 1:
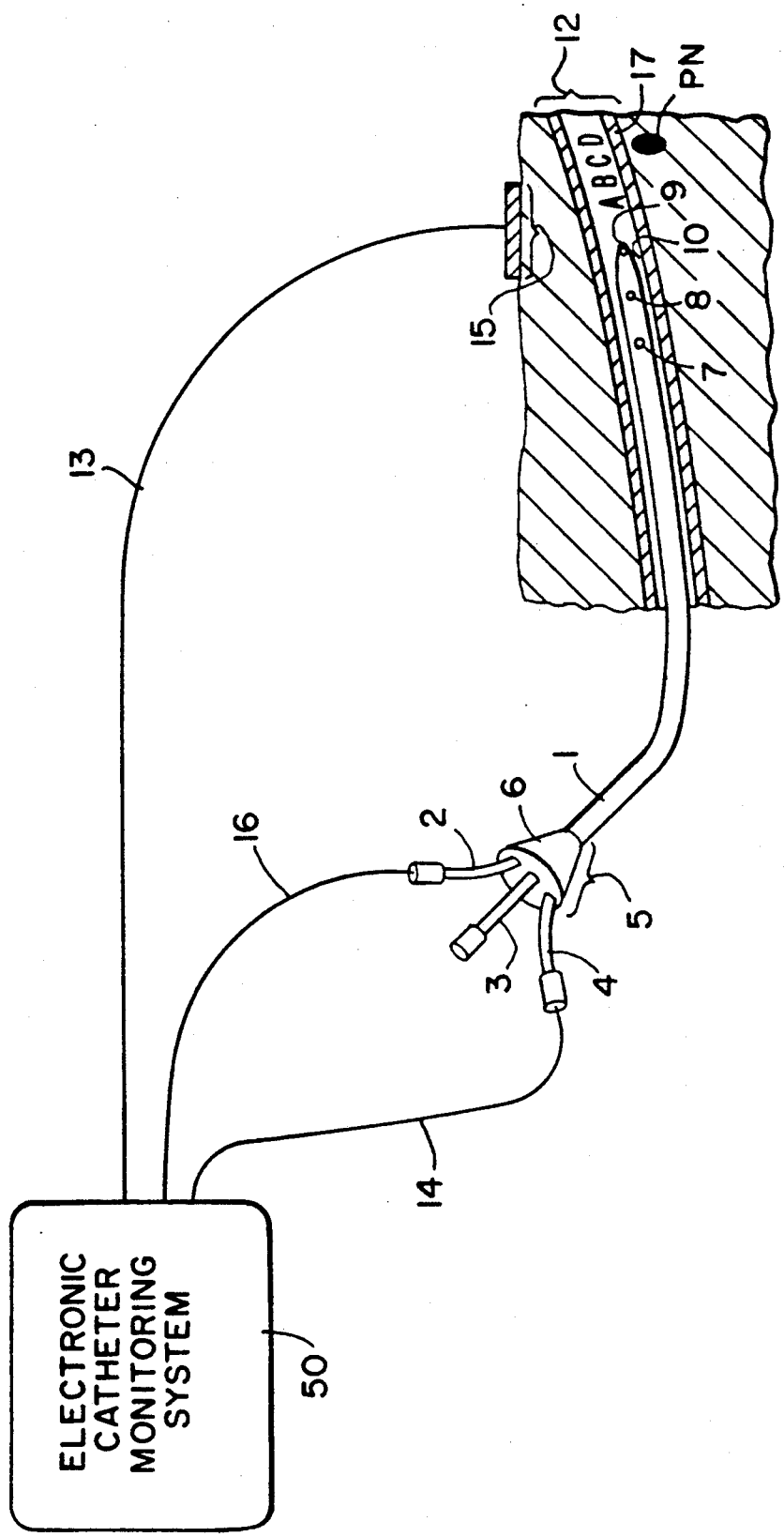
FIG. 1 is a schematic drawing of a catheter electronic monitoring system including a catheter having three lumens that are each capable of passing fluid to the body of the patient. Two transmission lines are positioned in two different lumens of the catheter terminating at the catheter distal tip at two different locations. The catheter is in tho process of being inserted into a vein of a patient, a third transmission line is in contact with the skin of the patient, and the electronic monitoring apparatus is operatively connected with the transmission lines.

Reference is now made specifically to the drawings in which identical or similar patts are designated by the same reference numerals throughout.

FIG. 1 illustrates a electronic catheter monitoring system 50. Electronic catheter 1 having three lumens, lumens 2 and 3 and distal lumen 4 positioned within the tubular interior of catheter 1 and extending from the proximal end 5 of catheter 1 where a mounting tie 6 can if desired be used to grip lumens 2, 3, 4. Lumens 2, 3, and 4 are capable of passing lumen fluid to the body of the patient. Catheter 1, which is configured as a tubular member having generally flexible walls made of a non-electrically conductive bio-compatible material such as plastic defines side openings 7, 8, which open at the side wall of catheter 1 spaced apart at catheter distal end 10, and distal opening 9, which opens at the distal tip 10 of catheter 1. Lumens 2 and 3 extend to and open coextensive with side openings 7 and 8, respectively, and lumen 4 extends to and opens coextensive with distal opening 9.

FIG. 1 illustrates the electronic catheter monitoring system 50 for assisting in the placement of a medical device into the body 11 of a patient to a specific site. Electronic catheter monitoring system 50 may include an analog digital converter, and a switching matrix. The electronic catheter monitoring system 50 may include a computer and may have a printer or a video monitor or an audio speaker. Electronic catheter monitoring system 50 is in circuit with electronic catheter 1 in the process of being inserted into a blood vessel 12 near the region of a pacemaker node PN, each schematically illustrated. The pacemaker node PN is located near the wall of the blood vessel 12. A transmission line 13 extends external to the skin of body 11 to be attached anywhere on the body with transmission contact area located at 15. Transmission line 14 passes through lumen 4 to distal end 10 of catheter 1 and ends with it's transmission contact area located at opening 9. Transmission line 16 passes through lumen 2 to distal end 10 of catheter 1 and end with it's transmission contact area located at opening 7. The electrical catheter monitoring system 50 monitors the pacemaker generated electrical potentials of body tissue encountered between transmission contact area 9 located before A and transmission contact area located at 7 and/or the transmission contact area located at 15.

The electronic catheter monitoring system 50 which is in circuit with the electrical catheter 1 includes an optional analog/digital converter as well as an optional switching matrix. This device may also include a computer to allow for the programming of its functioning. The various components may be manually operated or alternatively they ma be controlled by each other or the computer component. They are described as follows:

The analog digital converter (optional) functions in the conversion of monitored analog electronic signals into digital signals and as such includes a required filtering system. Such digital signals may be converted into alpha/numeric messages to be displayed by the electronic catheter monitoring system 50.

The optional switching matrix component of the electronic catheter monitoring system 50 may electronically or mechanically switch the connections between this system and the various transmission lines.

The electronic catheter monitoring system 50 may be portable and battery operated.

The monitor control system 55 may be manually operated or it may be computerized, and may have a print out or a monitor. Electrical monitors may include such specialized equipment as electrical analyzers or a custom designed electric characteristic monitor. It can be a EKG machine, or a standard multi-meter which indicates voltage, current, or impedance; or a standard oscilloscope. The electrical characteristic monitor can be a voltage meter which can measure in both the time and frequency domain. It may include filters if necessary.

For the monitoring of electric signals a minimum of two a minimum of two transmission lines to the electronic catheter is required by the electronic catheter monitoring system 50.

An application of the electrical catheter monitoring system 50 is to monitor and characterize the electrical characteristics of body tissue located between at least two transmission line . transmission contact areas, where one of these transmission contact areas 9 is located at the tip 10 of the electrical catheter transmission lines (as described).

The following is a description of the application of the present invention when employed for the monitoring and/or evaluation of low frequency electrical signals:

The transmission lines 13, 14 an 16 transmit electrical signals between their tissue contact areas 15, 9 and 7 to the electronic catheter monitoring system 50. The monitored electronic signals generated from the body pacemaker node tissue PN between transmission contact area 9 and transmission contact area 15 or transmission contact area 7 as the catheter end 10 is moved through blood vessel 12 can be determined by many methods. Continuous values of voltage or current can be sent to electronic catheter monitoring system 50 so that encountered potentials during the electrical catheter 1 insertion process can be measured or implied. Electronic catheter monitoring system 50 evaluates the monitored signal and displays its characterization or evaluation of the monitored endogenous pacemaker electrical signals between the various transmission contact area's as the electrical catheter 1 is moved through body 11 or blood vessel 12.

For example, during electronic catheter 1 insertion within a blood vessel 12 the monitored electrical characteristics of the bodies pace maker node PN may continuously change in accordance with the movement of the catheter 1. As a result of this movement the absolute monitored electrical characteristics, that is, the measured pacemaker PN electrical signal of the tissue between the transmission contact area located at 9 and transmission contact areas located at 7 and/or 15 will change. Both the absolute and relative values of the monitored electrical characteristics are of significance to the present invention. This is true because the pacemaker potentials measured through the body tissue II may be of significance primarily as relative values, that is, whether or not the potential suddenly rises or falls. A sudden monitored pacemaker potential increase could indicate that the transmission contact area located at 9, for example, has come in close proximity of the monitored pacemaker node PN. Another sudden return to the previous monitored potential amplitude thereafter associated with a movement of the electrical catheter 1 would indicate that distal tip 10 of the is no longer close to the pacemaker node PN as it has moved away from this location while traveling along the blood vessel 12. Monitored pacemaker potentials from the tip of the catheter 1 transmission contact area 9 are displayed on the electronic catheter monitoring system 50 to signal conditions to either go-ahead or caution or stop to the physician for the placement of the electrical catheter. That is, the physician will make decisions based on the displayed output from electronic catheter monitoring system 50 as absolute values or relative values just prior to the currently displayed values. Although the electrical characteristics of the body tissue or both are actually measured between the various transmission contact areas 9 and 7 or 15 in FIG. 1, nonetheless any significant changes in the electrical characteristics being displayed at monitor control system 55 are the result of local electrical characteristics of body tissue encountered at the transmission contact area located at 9. This is possible, for example when monitoring pace maker node electrical characteristics, by employing two different size transmission contact areas or by the positioning of transmission contact areas, for example, 9 (in blood) and 15 (on skin) such that there is a significant difference in their electrical resistances or impedances. The law of averages enables the higher resistance to dominate over the lower resistance. For example, where the first transmission line contact area measures 5 cm × 5 cm (25 cm) and is located on the skin of the chest and the second transmission line contact area measures 0.05 cm$^2$ and is located at the tip of an insulated hypodermic syringe needle in a vein, the second conductor has a significantly higher resistance than the first. The monitored potentials from the tissue located at the tip of the needle will be the dominant pacemaker node generated voltage potentials that can be measured by the electronic catheter monitoring system 50 in this example.

The embodiment of the electronic catheter monitoring system 50 is to monitor endogenous electrical potentials to assist in the placement of electronic catheter 1 into body 11 of the patient to a specific site. The following example illustrates this embodiment of the electronic catheter monitoring system 50 in assisting in the placement of the catheter tip 10 in blood vessel 12, an then advancing the catheter 1 tip 10 from location A to location B within blood vessel 12 proximal (ie. before) location C (which is the closest site in the blood vessel 12 to the region of the region of the PN node). electrical potentials. The blood vessel 12 in FIG. 1 represents the major vein which passes adjacent to the PN node. In the practice of medicine, the optimal location for the placement of a tip of a catheter may be location B.

Figure 2A:
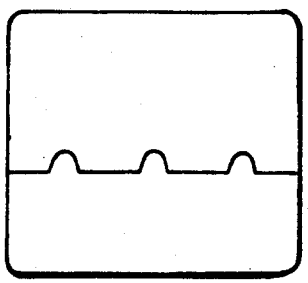

FIG. 2A, 2B, 2C, and 2D illustrate the monitored electrical potentials from the PN node displayed by electronic catheter monitoring system 50 in FIG. 1 as electrical catheter tip 10 is advanced distally into blood vessel 12 placing the transmission contact area located at 9 in the following locations within blood vessel 12: A, B, C, and D. At location A the monitored PN potential has the lowest amplitude (FIG. 2A).

Figure 2B:
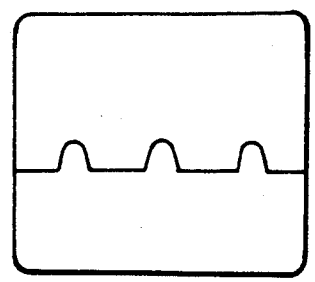
Figure 2C:
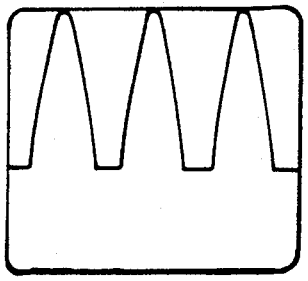
Figure 2D:
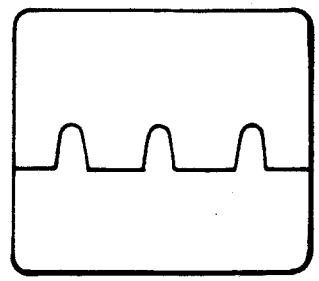

At location C the monitored PN potential has the highest amplitude (FIG. 2C). The amplitude of the PN potential at location C (FIG. 2C) is greater than the monitored PN potential at locations A or B or D (FIGS. 2A, 2B, and 2D). Thus, the electronic catheter monitoring system 50 may indicate by a continuous readout the increasing or decreasing intensity of the PN potential emitted by the PN node that the transmission contact area located at 9 transmits as it is approaching or moving away from the PN pacemaker node. This information is used to assist the physician in guiding the electrical catheter 1 to a final position B in proximity to the PN pacemaker node and confirm its placement.

Figure 3:
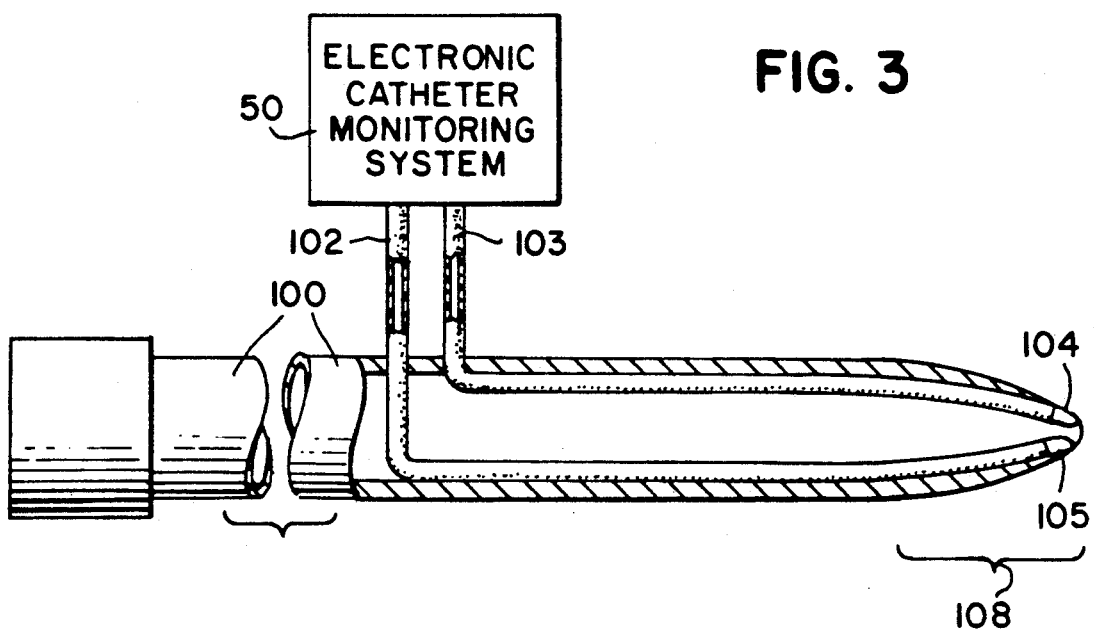
FIG. 3 illustrates electrical catheter monitoring system as may be applied for standard syringe needle application, using more than one conductor in the needle.

FIG. 3 illustrates the electronic catheter monitoring system 50 as may be applied for standard syringe application. In this application the metal syringe needle 100 serves as the electrical catheter. The needle 100 has two insulated transmission lines 102 and 103 that course along its length. The proximal ends of transmission lines 102 and 103 are connected with the electronic catheter monitoring system 50. The electronic catheter monitoring system 50 is analogous to the electronic catheter monitoring system 50 described in FIG. 1. The distal ends of the transmission lines are uninsulated and are located at the tip 108 of the needle 100 The uninsulated end 104 of transmission line 103 serves as the transmission contact area for transmission line 103 The uninsulated end 105 of transmission line 102 serves as the transmission contact area for transmission line 102. The electronic catheter needle 100 is configured with transmission lines 102 and 103 to permit the electronic catheter monitoring system 50 to monitor and evaluate the electric characteristics of tissue in contact with transmission contact areas 104 and 105 as the needle 100 is inserted into tissue.

Figure 4:
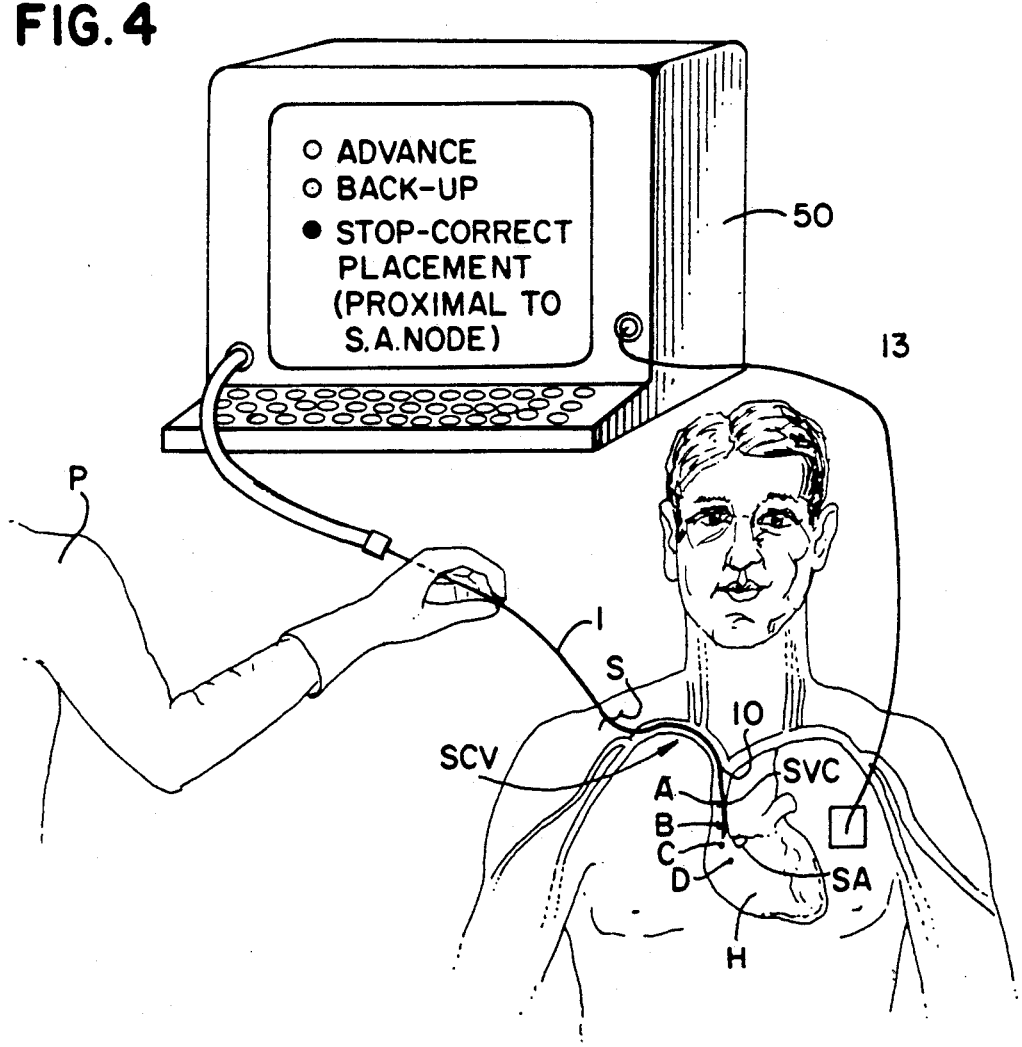
FIG. 4 illustrates electrical catheter monitoring system as may be applied in the clinical placement localization by characterization of monitored cardiac sino-atrial (SA) pacemaker node potentials in the localization of an electrical catheter near the SA pacemaker node of tho heart.

FIG. 4 illustrates the electronic catheter monitoring system 50 as may be applied in the clinical localization by characterization of monitored cardiac sino-atrial SA pacemaker node potentials in the localization for placement of an electrical catheter tip 10 within the superior vena cava SVC referenced to the SA pacemaker node of the heart H. The electrical catheter monitoring system 50 is similar to the system 50 described in FIG. 1. The electronic catheter 1 is being inserted by a physician P through the patients skin S and right subclavian vein SCV along the superior vena cava SVC. The following example illustrates this embodiment of the electrical catheter monitoring system 20 in assisting in the placement of the catheter tip 10 is blood vessel SVC, and then advancing the catheter 1 tip 10 from location A to location B within blood vessel SVC, to location C which is the closest site in the blood vessel SVC to the region of the region of the SA node. The SA node generates electrical pacemaker potentials. The blood vessel SVC in FIG. 4 represents the major vein which passes adjacent to the SA node. In the practice of medicine, the optimal location for the placement of a tip of a catheter is location B, ie. in the superior vena cava SVc immediately proximal to the sinoatrial SA node. This location B is desired because it has the greatest volume of venous blood flow in the body outside the heart which makes it the safest place in the circulatory system to administer medications.

Figure 5A:
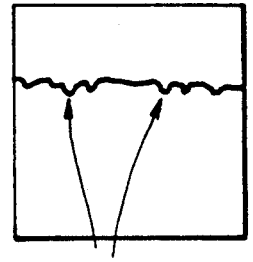
FIGS. 5A, 5B, 5C, and 5D illustrate the electrocardiogram (EKG) electrical potentials, known as P WAVES potentials from the cardiac SA pacemaker node as monitored by the electrical catheter monitoring system 50 in FIG. 4 as electrical catheter tip 10 is advanced distally into blood vessel SVC placing tho transmission contact area located at the catheter tip 10 in the following locations within blood vessel SVC A, B, C and D.
Figure 5B:
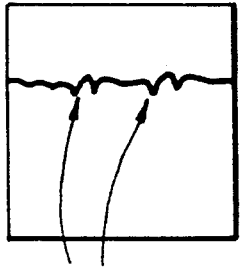
Figure 5C:
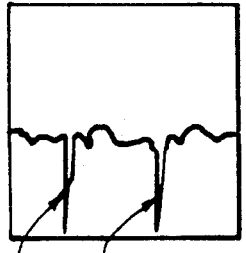
Figure 5D:
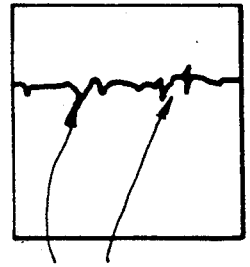

FIGS. 5A, 5B, 5C, and 5D illustrate the monitored electrical EKG potentials, known as P WAVES from the SA node (illustrated in FIG. 1) monitored by the electrical catheter monitoring system 50 in FIG. 4 as electrical catheter tip 10 is advanced distally into blood vessel SVC placing the transmission contact area located at the catheter tip 10 in the following locations within blood vessel SVC: A, B, C and D. At location A the monitored SA P-WAVE potential has the lowest amplitude (FIG. 5A). At location C the monitored PN P-WAVE potential has the greatest amplitude (FIG. 5C). The amplitude of the PN P-WAVE potential at location C (FIG. 5C) is greater than the monitored PN potential at locations A or B or D (FIGS. 5A and 5B). Thus, the electrical catheter monitoring system 50 will evaluate the P-WAVE during the insertion of the electrical catheter 1 as the tip of the catheter moves from location A to D. During the movement of the catheter tip 10 from location A to C the electrical catheter monitoring system 50 will detect an increasing intensity of the P-WAVE, which indicates that the catheter tip 10 is approaching the SA node. During the approach of the catheter tip towards the SA node the electrical catheter monitoring system 50 indicates to the physician P, inserting of the electrical catheter 1, to continue advancing the electronic catheter 1. As the tip of the catheter 10 moves from location C towards location D the electrical catheter monitoring system 50 will detect a decrease in the intensity of the P-WAVE, which indicates that the catheter tip 10 is going away from or moving beyond the SA node. During the movement of the catheter tip 10 beyond the SA node the electrical catheter monitoring system 50 indicates to the physician P to backup or reverse the movement of the electronic catheter 1. During the reversal of the movement of the catheter the electrical catheter monitoring system 50 will continue to evaluate the P-WAVES. An evaluation algorithm, which is a sequential formula, is employed by the electronic catheter monitoring system 50 that will notice that there is an increasing monitored potential and they will notice that it decreases. By recognizing this relationship it will indicate on its display "BACK UP". While the physician P is backing up the placement of the electronic catheter I the electronic catheter monitoring system 50 will discern that the monitored potential increases and then starts to decrease. When the monitored potential then decreases during backward catheter movement by a certain percentage as determined by the electronic catheter monitoring system 50 the system display will indicate "STOP", thereby indicating that the catheter tip 10 is in the correct location. The electronic catheter monitoring system 50 thereby functions to recognize that as the catheter tip 10 moves from location D to location B the monitored P-WAVES will again reach their maximum potential at location C and then start to decrease as the catheter tip approaches location B. This algorithm is programed to detect a predetermined percentage decrease in the p-WAVE potentials as the catheter tip 10 moves from location C to location B and at such a value trigger the monitor to indicate to the physician P to stop movement of the catheter 1— as it is now in the correct location. The correct or safe location is the place before the maximum potential is reached.

There may be variations of the above designs in FIGS. 1, 3 and 4.

The present invention includes a method of placing a device such as a catheter or probe subcutaneously within the body or tissue of a patient comprising the following steps:
   a) Implanting a catheter or probe having distal ends subcutaneously into the body of a patient;
   b) Monitoring the electrical characteristics of the tissue at the tip of the catheter.
   c) Using the information from step b above to guide the advancement of the catheter within the body towards a specific site in the body while monitoring the electrical characteristics of the tissue in contact with the tip of the catheter.
   d) Terminating the advance of the catheter into the body when the distal end of the catheter is at the specific site as determined by information provided by the catheter monitoring system based on an analysis of endogenous electrical signals monitored from the tip of the catheter.

Although the present invention has been described in some detail by way of illustration and example for purposes of clarity and understanding, it will, of course, be understood that various changes and modifications may be made with the form, details, and arrangements of the parts without departing from the scope of the invention as set forth in the following claims.

What is claimed is:

1. The method for locating a catheter within a body circulatory vessel referenced to a natural pacemaker node of the heart comprising the steps of advancing a catheter tip within a body circulatory vessel toward a pacemaker node while monitoring the natural pacemaker node potentials which increase as the node is approached and decrease as the node is passed, halting or reversing the direction of the catheter tip when the monitor potential changes from a relative or absolute maximum value to a less than maximum value and pulling the catheter tip back until the maximum value is again monitored and then continuing the pulling back of the catheter tip to a place which is definitely before the place of monitored maximum potential, and whereby this method also serves to permit monitoring and confirmation of said catheter tip location.

2. The method in accordance of claim 1 and administering a nutrient through said catheter when the tip is in said definite place.

3. The method in accordance of claim 1 and administering a pain killing medication through said catheter when the tip is in said definite place.

4. The method in accordance of claim 1 and administering a drug for normalizing an abnormal condition through said catheter when the tip is in said definite place.

5. The method in accordance of claim 1 and removing a substance from the body through said catheter when the tip is in said definite place.

6. The method for locating a catheter within a major vein referenced to an anatomically natural pacemaker node of the heart comprising the steps of advancing a catheter tip within a vein toward an anatomically natural pacemaker node while monitoring the natural pacemaker node voltage which increases as the node is approached through the vein and decreases as the node is passed in the vein, halting or reversing the direction of the catheter tip in the vein when the monitored voltage changes from a relative or absolute maximum value to a less than maximum value and pulling the catheter tip back until the maximum value is again monitored and then continuing the pulling back of the catheter tip to a place which is definitely before the place of monitored maximum voltage, whereby this method also serves to permit monitoring and confirmation of said catheter tip location with reference to an anatomically natural pacemaker node.

* * * * *